United States Patent
Kamei

(10) Patent No.: US 9,242,949 B2
(45) Date of Patent: Jan. 26, 2016

(54) METHOD FOR PRODUCING ALKANEDIOL MONOGLYCIDYL ETHER (METH)ACRYLATE

(71) Applicant: HITACHI CHEMICAL COMPANY, LTD., Tokyo (JP)

(72) Inventor: Junichi Kamei, Chiba (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 0 days.

(21) Appl. No.: 14/399,553

(22) PCT Filed: Apr. 25, 2013

(86) PCT No.: PCT/JP2013/062238
§ 371 (c)(1),
(2) Date: Nov. 7, 2014

(87) PCT Pub. No.: WO2013/168586
PCT Pub. Date: Nov. 14, 2013

(65) Prior Publication Data
US 2015/0094478 A1    Apr. 2, 2015

(30) Foreign Application Priority Data

May 11, 2012  (JP) ................. 2012-109481

(51) Int. Cl.
*C07D 301/27* (2006.01)
*C07D 301/28* (2006.01)
*C07D 301/00* (2006.01)
*C07D 303/24* (2006.01)

(52) U.S. Cl.
CPC ............ *C07D 301/28* (2013.01); *C07D 301/00* (2013.01); *C07D 303/24* (2013.01)

(58) Field of Classification Search
CPC ... C07D 301/00; C07D 301/28; C07D 303/24
USPC ........................................................ 549/516
See application file for complete search history.

(56) References Cited

U.S. PATENT DOCUMENTS 8,183,018 B2 * 5/2012 Haering et al. ................ 435/117
2010/0048927 A1   2/2010 Haering et al.

FOREIGN PATENT DOCUMENTS

| | | | |
|---|---|---|---|
| CN | 101528938 A | | 9/2009 |
| JP | 8-99968 A | | 4/1996 |
| JP | 2003-342268 A | | 12/2003 |
| JP | 2006241081 | * | 9/2006 |
| JP | 2010-507380 A | | 3/2010 |
| JP | 2010-222373 A | | 10/2010 |
| JP | 2013-23479 A | | 2/2013 |
| WO | 2006/093281 A1 | | 9/2006 |
| WO | 2008/032389 A1 | | 3/2008 |
| WO | 2008/049814 A1 | | 5/2008 |

OTHER PUBLICATIONS

Notification of Transmittal of Translation of the International Preliminary Report on Patentability mailed Nov. 20, 2014, for International Application No. PCT/JP2013/062238.
Communication mailed Jun. 16, 2015, for Chinese Application No. 201380024187.2, together with partial English language translation thereof, 9 pages.
Communication mailed Jun. 6, 2015, for Chinese Application No. 201380024187.2, together with partial English language translation thereof, 9 pages.

* cited by examiner

*Primary Examiner* — T. Victor Oh
(74) *Attorney, Agent, or Firm* — Fitch, Even, Tabin & Flannery LLP

(57) ABSTRACT

Provided is a production method which is capable of efficiently producing an alkanediol glycidyl ether (meth)acrylate with high purity and high yield without requiring a troublesome purification process. A method for producing an alkanediol glycidyl ether (meth)acrylate, which comprises: a step wherein a vinyloxyalkyl glycidyl ether is subjected to a devinylation reaction in the presence of an acid catalyst and water; and a subsequent step wherein an esterification reaction is carried out.

5 Claims, No Drawings

METHOD FOR PRODUCING ALKANEDIOL MONOGLYCIDYL ETHER (METH)ACRYLATE

TECHNICAL FIELD

The present invention relates to a method for producing an alkanediol monoglycidyl ether (meth)acrylate by eliminating a vinyl group from a vinyloxyalkyl glycidyl ether and then esterifying the product.

BACKGROUND ART

Alkanediol glycidyl ether (meth)acrylates are useful raw materials for paints, coatings, adhesives, and UV-curable resins for electronic materials. A conventional method for producing an alkanediol glycidyl ether (meth)acrylate usually includes allowing an alkanediol to react with an epihalohydrin in the presence of an alkali hydroxide to produce a complex of glycidyl ethers, subjecting the complex to purification processes such as extraction and distillation to yield an alkanediol monoglycidyl ether, and then subjecting the product to esterification reaction. In such a method, purification processes such as extraction with a solvent and distillation are essential, and finally, depending on the condition of the reaction and the purification, difunctional reactive group-containing compounds such as di(meth)acrylate and diglycidyl ether remain as impurities. When such a compound containing impurities is used in the production of paints, coatings, adhesives, or other materials, a crosslinking reaction often occurs, so that the desired properties cannot be obtained in many cases.

To solve the problems, studies have been made on purification methods for efficiently producing an alkanediol monoglycidyl ether (Patent Literatures 1 and 2). However, such methods have a problem such as insufficient removal of impurities or low yield.

CITATION LIST

Patent Literature

Patent Literature 1: JP 2003-342268 A
Patent Literature 2: JP 2010-222373 A

SUMMARY OF INVENTION

Technical Problem

It is an object of the present invention to provide a method capable of efficiently producing an alkanediol glycidyl ether (meth)acrylate with a high yield and a high purity without any need for complicated purification processes.

Solution to Problem

As a result of various investigations, the inventor has found that an alkanediol glycidyl ether (meth)acrylate can be produced with a high yield and a high purity by a short process that includes performing glycidylation of an alkanediol monovinyl ether to form a vinyloxyalkyl glycidyl ether, then eliminating the vinyl group in the presence of an acid catalyst and water to produce an alkanediol monoglycidyl ether, and then subjecting the product to an esterification reaction.

Specifically, the present invention is directed to the following.

(1) A method for producing an alkanediol glycidyl ether (meth)acrylate, the method including the steps of: subjecting a vinyloxyalkyl glycidyl ether to a devinylation reaction in the presence of an acid catalyst and water; and then performing an esterification reaction.

(2) The method according to item (1), further including the step of adding an aqueous acid solution to perform an acetal decomposition reaction between the step of performing the devinylation reaction and the step of performing the esterification reaction.

(3) The method according to item (1) or (2), further including the step of allowing a vinyl ether moiety-containing alcohol to react with an epihalohydrin to yield a vinyloxyalkyl glycidyl ether.

(4) The method according to item (3), wherein the vinyl ether moiety-containing alcohol is 4-hydroxybutyl vinyl ether.

The disclosure of the present application is related to the subject matter described in Japanese Patent Application 2012-109481 filed on May 11, 2012 in Japan, the disclosure of which is incorporated herein by reference.

Advantageous Effects of Invention

The present invention makes it possible to provide a method capable of efficiently producing an alkanediol glycidyl ether (meth)acrylate with a high yield and a high purity without using any complicated purification process such as distillation.

DESCRIPTION OF EMBODIMENTS

Hereinafter, embodiments of the method of the present invention of producing an alkanediol glycidyl ether (meth)acrylate will be described in detail.

The method of the present invention of producing an alkanediol glycidyl ether (meth)acrylate includes the steps of: subjecting a vinyloxyalkyl glycidyl ether to a devinylation reaction in the presence of an acid catalyst and water; and then performing an esterification reaction.

In the present invention, a vinyloxyalkyl glycidyl ether is a starting material. The vinyloxyalkyl glycidyl ether may be, for example, vinyloxybutyl glycidyl ether, vinyloxyhexyl glycidyl ether, vinyloxynonyl glycidyl ether, vinyloxydecanyl glycidyl ether, vinyloxydodecyl glycidyl ether, or the like.

Examples of an acid catalyst that may be used in the devinylation reaction according to the present invention generally include sulfuric acid, sodium hydrogen sulfate, p-toluenesulfonic acid, benzenesulfonic acid, methanesulfonic acid, and a solid acid (such as zeolite, amberlite, Amberlyst, or Nafion). The catalyst is preferably used in an amount of 0.1 to 10% by mass, more preferably in an amount of 0.5 to 2% by mass in view of reactivity, based on the amount of the vinyloxyalkyl glycidyl ether subjected to the reaction. The amount of the catalyst is preferably 0.1% by mass or more in order to increase the devinylation reactivity so that a sufficient reaction rate can be easily achieved. The amount of the catalyst is also preferably 10% by mass or less in order to suppress the production of an acetal dimer or by-products including products of ring-opening and polymerization of the glycidyl group.

In the devinylation reaction according to the present invention, water may be used in any amount equal to or greater than the molar amount of the vinyloxyalkyl glycidyl ether. Preferably, water is used in an amount of 20 to 60% by mass based on the amount of the vinyloxyalkyl glycidyl ether, so that the devinylation reaction can proceed quickly. The amount of water is preferably 20% by mass or more in order to suppress the production of an acetal dimer or by-products such as products of ring-opening and polymerization of the glycidyl group. The amount of water is preferably 60% by mass or less in order to increase the devinylation reactivity so that a sufficient reaction rate can be easily achieved.

The devinylation reaction according to the present invention is an exothermic reaction, and acetaldehyde produced by the reaction should be removed from the system under reduced pressure. The reaction temperature may be controlled at 60° C. or less, preferably 20 to 50° C., so that gelation or by-product formation can be prevented and an alkanediol monoglycidyl ether can be obtained with a high purity. The reaction temperature may be controlled by a method of cooling the reaction vessel or a method of gradually adding the vinyloxyalkyl glycidyl ether to an aqueous catalyst solution. After the completion of heat generation, the temperature should be maintained by heating with a warm bath or other means. When the reaction temperature is in the range of 20 to 50° C., the pressure in the reaction system may be reduced to 50 kPa or less so that acetaldehyde can be removed from the system. The pressure in the system is more preferably 30 kPa or less so that the devinylation reaction can be efficiently carried out.

Acetaldehyde produced during the devinylation reaction can be removed as described above. However, acetaldehyde can be partially absorbed into water and react with the alkanediol monoglycidyl ether, which is produced by the devinylation reaction, to form an alkanediol monoglycidyl ether methyl acetal (acetal dimer). This acetal dimer-forming reaction is reversible, and the acetal dimer can be easily decomposed in the presence of an acid catalyst. Therefore, after the devinylation reaction is completed and before the esterification reaction is started, an aqueous acid solution may be added so that the acetal dimer can be decomposed by an acetal decomposition reaction.

When the acetal decomposition reaction is performed, the aqueous acid solution used may be an aqueous solution of any of the acids listed above in the description of the acid catalyst. In this case, the aqueous acid solution is added preferably, but not necessarily, in an amount of 0.1 to 10% by mass based on the amount of the vinyloxyalkyl glycidyl ether. The concentration of the aqueous acid solution is preferably, but not limited to, 0.01 to 5% by mass. When the amount and concentration of the acid in the acetal decomposition reaction fall within the ranges, the decomposition reaction can be performed at a higher rate, and the production of by-products can be suppressed.

To perform the acetal decomposition reaction according to the present invention, the aqueous acid solution may be added either at once or gradually dropwise. The pressure conditions of the devinylation reaction may be continuously used in the acetal decomposition reaction system. In order for the acetal decomposition reaction to proceed quickly, however, the pressure in the reaction system is preferably 20 kPa or less, more preferably 10 kPa or less.

After the reaction is completed, the acid catalyst should be neutralized with a base so that it can be separated and removed. The base may be, for example, a hydroxide or salt of an alkali or alkaline earth metal, such as potassium hydroxide, sodium hydroxide, potassium carbonate, sodium carbonate, potassium hydrogen carbonate, or sodium hydrogen carbonate. After the neutralization, the aqueous layer is separated and removed. In this process, to improve the separation ability, solvents such as toluene, xylene and so on may be used alone or in combination of two or more, and a method of adding sodium chloride or the like to increase the specific gravity of the aqueous layer may also be used.

After the neutralization, concentration is performed in which excess water and, if used, the solvent are removed by distillation. The concentration is preferably performed under normal or reduced pressure with the liquid temperature being kept at 90° C. or less, more preferably in the range of 65° C. to 85° C. When the liquid temperature is kept at 90° C. or less, the alkanediol monoglycidyl ether can be prevented from undergoing coloration or decomposition.

After the concentration, filtration may be performed to remove insoluble residues such as the neutralized salt. In the filtration, a filter aid such as diatomaceous earth is preferably used to remove the insoluble matter efficiently.

According to the present invention, an alkanediol monoglycidyl ether can be produced through the devinylation reaction in the presence of water and optionally the acetal decomposition reaction. Therefore, the process of producing the alkanediol monoglycidyl ether according to the present invention does not require any purification step other than the filtration. In some cases, however, common purification methods such as distillation may be performed.

In the present invention, an esterification reaction is performed to produce an alkanediol glycidyl ether (meth)acrylate. The esterification reaction may be a dehydration esterification reaction or an acid halide reaction. More preferably, the esterification reaction is a transesterification reaction between the alkanediol monoglycidyl ether and an alkyl (meth)acrylate, which is the most convenient and high-yield reaction.

The alkyl (meth)acrylate used in the transesterification reaction according to the present invention may be, for example, a lower (meth)acrylic ester such as methyl (meth)acrylate, ethyl (meth)acrylate, propyl (meth)acrylate, or butyl (meth)acrylate. In the present invention, the lower (meth) acrylic ester has four or less carbon atoms in its alkyl group bonded to its (meth)acryloyl group.

In the reaction, the lower (meth)acrylic ester is preferably used in an excess amount relative to the alkanediol monoglycidyl ether, so that the reaction can be performed in a shorter time with a higher conversion degree and the post-treatment after the reaction can be simple. More specifically, the lower (meth)acrylic ester is preferably used in an amount of 2.0 to 30 moles relative to the alkanediol monoglycidyl ether. When the lower (meth)acrylic ester is used in an amount of 2.0 to 30 moles, a higher reaction rate can be achieved, and the concentration process after the reaction can be completed in a shorter time, so that higher productivity can be achieved.

A catalyst is used in the transesterification reaction. Examples of such a catalyst include an alkali metal hydroxide such as lithium hydroxide, sodium hydroxide, or potassium hydroxide, an alkali metal carbonate such as lithium carbonate, sodium carbonate, or potassium carbonate, an alkali metal alkoxide such as lithium methoxide, sodium methoxide, sodium ethoxide, or potassium tert-butoxide, an alkali metal amide such as lithium amide, sodium amide, or potassium amide, a titanium alkoxide such as tetramethyl orthotitanate, tetraethyl orthotitanate, tetrapropyl orthotitanate, tetraisopropyl orthotitanate, or tetrabutyl orthotitanate, and others such as aluminum alkoxide and tin alkoxide. In particular, a titanium alkoxide is more preferred because side reactions can be minimized with it and the catalyst can be easily removed with water added after the reaction is completed.

Generally, in the transesterification reaction, the catalyst is preferably used in an amount of 0.2 to 15% by mass based on the total amount of the lower (meth)acrylic ester and the raw material alcohol. When the amount of the catalyst is from 0.2 to 15% by mass, the reaction can proceed quickly, and the residue produced when the catalyst is deactivated can be easily removed, so that higher productivity can be achieved.

In the transesterification reaction, any suitable solvent not capable of being involved in the reaction may also be used. Examples of solvents that may be used include hydrocarbons such as benzene, toluene, xylene, hexane, heptane, octane, isooctane, and cyclohexane, and ethers such as dioxane.

In the esterification reaction according to the present invention, a known polymerization inhibitor is preferably added and used in combination with other materials. Examples of such a polymerization inhibitor include phenols such as hydroquinone and hydroquinone monomethyl ether, sulfur compounds such as phenothiazine and ethylene thiourea, copper salts such as copper dibutyldithiocarbamate, manganese salts such as manganese acetate, nitro compounds, nitroso compounds, and N-oxyl compounds such as 4-hydroxy-2,2,6,6-tetramethylpiperidinoxyl. The polymerization inhibitor is preferably added in an amount of 0.2% by mass or less based on the amount of the produced ester. If the amount is more than 0.2% by mass, the additive may cause coloration.

After the reaction is completed, washing with water is performed to remove the catalyst. When a titanium alkoxide is used as the catalyst, the catalyst can be deactivated by adding water, and the excess lower (meth)acrylic ester and water can be removed at the same time using a concentrator.

In the concentration, low-boiling-point components are preferably removed by distillation under normal or reduced pressure with the liquid temperature being kept at 90° C. or less, more preferably 80° C. or less, even more preferably in the range of 50 to 70° C. When the liquid temperature is 90° C. or less, coloration or polymerization of the (meth)acrylic ester can be suppressed.

On the other hand, in the present invention, the vinyloxyalkyl glycidyl ether is preferably obtained by glycidylation of the hydroxyl group of an alkanediol monovinyl ether. If an acid catalyst is used, a glycidylation reaction process cannot be adapted due to the reaction of the vinyl group. If an alkali metal hydroxide is used for a reaction with an epihalohydrin, a common glycidylation reaction process can be used.

The alkanediol monovinyl ether may be, for example, 4-hydroxybutyl vinyl ether, 6-hydroxyhexyl vinyl ether, 9-hydroxynonyl vinyl ether, 10-hydroxydecanyl vinyl ether, 12-hydroxydodecyl vinyl ether, or the like.

An alkali metal hydroxide is used in the glycidylation reaction according to the present invention. Such an alkali metal hydroxide is, for example, but not limited to, potassium hydroxide, sodium hydroxide, or the like. The alkali metal hydroxide should be used in an amount of one equivalent or more, preferably one to two equivalents, relative to the alkanediol monovinyl ether. When one equivalent or more of the alkali metal hydroxide is used, the reaction will not stop in the middle of the process, and side reactions will be less likely to occur, so that purity deterioration can be prevented.

The epihalohydrin used in the present invention is preferably epichlorohydrin, which is easily available. The epihalohydrin should be used in an amount of one equivalent or more, preferably 1 to 10 equivalents, relative to the alkanediol monovinyl ether. When 1 to 10 equivalents of the epihalohydrin is used, the reaction will not stop in the middle of the process, and side reactions will be less likely to occur, so that purity deterioration can be prevented.

In the glycidylation reaction, a catalyst such as a quaternary ammonium salt may also be used. A common quaternary ammonium salt may be used, such as benzyltrimethylammonium chloride, benzyltriethylammonium chloride, tetramethylammonium chloride, or tetraethylammonium chloride.

After the vinyloxyalkyl glycidyl ether is obtained by the glycidylation reaction, purification by distillation may be further performed. In general, the method of purification by distillation is preferably distillation under reduced pressure although it depends on the boiling point of the vinyloxyalkyl glycidyl ether.

EXAMPLES

Hereinafter, the present invention will be more specifically described with reference to examples, which however are not intended to limit the present invention.

Example 1

Synthesis of Vinyloxybutyl Glycidyl Ether

A 3-L cylindrical flask equipped with a stirrer, a thermometer, and a dropping funnel was charged with 1,000 g (8.61 moles) of 4-hydroxybutyl vinyl ether (HBVE manufactured by Maruzen Petrochemical Co., Ltd.) and 448 g (11.2 moles) of sodium hydroxide. After the temperature of the mixture was raised to 40° C. with stirring, 1.243 g (13.4 moles) of epichlorohydrin was gradually added to the mixture and allowed to react at a temperature controlled to 40 to 60° C. After the reaction for 8 hours, sodium chloride produced by the reaction was removed by filtration. Subsequently, after 1,000 g of hexane was added to the reaction mixture, the mixture was washed with 400 g of a 3% sodium hydrogen sulfate aqueous solution and then 800 g of a 17% sodium chloride aqueous solution. The organic phase was concentrated using a rotary evaporator so that the hexane was removed by distillation. The concentrate was filtered, so that the desired product, vinyloxybutyl glycidyl ether, was obtained with a purity of 96% and a yield of 92%.

Synthesis of Butanediol Monoglycidyl Ether

A 1-L four-necked separable flask was charged with 5.0 g of sodium hydrogen sulfate and 140 g of pure water and then provided with a stirrer, a thermometer, an air-introducing tube, and a vacuum pump with a cooling trap. With stirring, 500 g of vinyloxybutyl glycidyl ether synthesized as described above was gradually added to the flask while the liquid temperature was controlled to be kept at 40° C. After the addition was completed, the pressure was reduced to 20 kPa. The mixture was continuously stirred for 1 hour while dry air was introduced at 100 ml/minute. The reaction liquid was then analyzed by gas chromatography. As a result, no peak was observed for vinyloxybutyl glycidyl ether, and thus, the reaction was completed. After 2.1 g of sodium hydrogen carbonate was added to neutralize the completed reaction liquid, the liquid was concentrated by removing water from the system by distillation using a rotary evaporator. After it was checked that the content of water in the system was 800 ppm or less, the liquid concentrate was filtered and then subjected to distillation (0.4 kPa, distillation temperature 82° C.) using a reduced-pressure distillation apparatus with a Vigreux column, so that butanediol glycidyl ether was obtained with a purity of 99% and a yield of 94%.

Synthesis of Butanediol Monoglycidyl Ether Acrylate

A 1-L flask equipped with a stirrer, a thermometer, an air-introducing tube, and a 15-stage rectifying tower was charged with 250 g of butanediol glycidyl ether synthesized as described above, 500 g of ethyl acrylate, and 0.1 g of p-methoxyphenol. While the pressure was controlled to 40 kPa and dry air was blown into the flask at a rate of 100 ml/minute, water was removed under reflux by heating until the content of water in the system reached about 300 ppm. Subsequently, 10 g of titanium tetraisopropoxide was added to start a reaction. During the reaction, the pressure in the system was controlled so that the reaction liquid temperature was about 95° C. The reaction was performed while the temperature of the top of the rectifying tower (tower top temperature) was monitored and while ethanol being produced and ethyl acrylate were removed as an azeotrope by distillation with the reflux ratio controlled at the azeotropic temperature of ethanol and ethyl acrylate. After 4 hours, the reaction liquid was sampled and subjected to gas chromatography analysis. As a result, the area percentage of butanediol monoglycidyl ether acrylate to butanediol monoglycidyl ether was 99.3% (degree of conversion), and thus, the reaction was completed. After the reaction liquid was cooled, 30 g of water was added to hydrolyze the catalyst. The reaction liquid was then transferred into a 1-L eggplant-shaped flask. The excess ethyl acrylate and water was removed by distillation under reduced pressure using a rotary evaporator. The product was then purified by suction filtration, so that the desired product, butanediol monoglycidyl ether acrylate, was obtained with a purity of 98.6% and a yield of 97%. At the time, the resulting product contained 0.7% of butanediol monoglycidyl ether, 0.02% of butanediol monoacrylate, and 0.01% of butanediol diacrylate.

Example 2

Synthesis of Butanediol Monoglycidyl Ether Methacrylate

The same procedure was performed as in Example 1, except that methyl methacrylate was used instead of ethyl acrylate. As a result, butanediol monoglycidyl ether methacrylate was obtained with a purity of 98.9% and a yield of 97%. At the time, the resulting product contained 0.4% of butanediol monoglycidyl ether, 0.03% of butanediol monoacrylate, and 0.01% of butanediol dimethacrylate.

Example 3

Synthesis of Butanediol Monoglycidyl Ether

A 1-L four-necked separable flask was charged with 5.0 g of sodium hydrogen sulfate and 140 g of pure water and then provided with a stirrer, a thermometer, an air-introducing tube, and a vacuum pump with a cooling trap. With stirring, 500 g of vinyloxybutyl glycidyl ether synthesized in Example 1 was gradually added to the flask while the liquid temperature was controlled to be kept at 40° C. After the addition was completed, the pressure was reduced to 20 kPa. The mixture was continuously stirred for 1 hour while dry air was introduced at 100 ml/minute. The reaction liquid was then analyzed by gas chromatography. As a result, no peak was observed for vinyloxybutyl glycidyl ether. Subsequently, 26 g of a 0.04% sodium hydrogen sulfate aqueous solution was added to the reaction liquid. While the temperature was kept at 40° C., the mixture was subjected to an acetal decomposition reaction at a pressure of 5 kPa. After 1 hour, the reaction was completed. After 2.1 g of sodium hydrogen carbonate was added to neutralize the completed reaction liquid, the liquid was concentrated by removing water from the system by distillation using a rotary evaporator. After it was checked that the content of water in the system was 800 ppm or less, the liquid concentrate was filtered and then subjected to distillation (0.4 kPa, distillation temperature 82° C.) using a reduced-pressure distillation apparatus with a Vigreux column, so that butanediol glycidyl ether was obtained with a purity of 99% and a yield of 94%. At the time, the resulting product contained 0.03% of butanediol, and no acetal dimer was detected.

Synthesis of Butanediol Monoglycidyl Ether Acrylate

A 1-L flask equipped with a stirrer, a thermometer, an air-introducing tube, and a 15-stage rectifying tower was charged with 250 g of butanediol glycidyl ether synthesized as described above, 500 g of ethyl acrylate, and 0.1 g of p-methoxyphenol. While the pressure was controlled to 40 kPa and dry air was blown into the flask at a rate of 100 ml/minute, water was removed under reflux by heating until the content of water in the system reached about 300 ppm. Subsequently, 10 g of titanium tetraisopropoxide was added to start a reaction. During the reaction, the pressure in the system was controlled so that the reaction liquid temperature was about 95° C. The reaction was performed while the temperature of the top of the rectifying tower (tower top temperature) was monitored and while ethanol being produced and ethyl acrylate were removed as an azeotrope by distillation with the reflux ratio controlled at the azeotropic temperature of ethanol and ethyl acrylate. After 4 hours, the reaction liquid was sampled and subjected to gas chromatography analysis. As a result, the area percentage of butanediol monoglycidyl ether acrylate to butanediol monoglycidyl ether was 99.3% (degree of conversion), and thus, the reaction was completed. After the reaction liquid was cooled, 30 g of water was added to hydrolyze the catalyst. The reaction liquid was then transferred into a 1-L eggplant-shaped flask. The excess ethyl acrylate and water was removed by distillation under reduced pressure using a rotary evaporator. The product was then purified by suction filtration, so that the desired product, butanediol monoglycidyl ether acrylate, was obtained with a purity of 98.6% and a yield of 97%. At the time, the resulting product contained 0.7% of butanediol monoglycidyl ether, 0.02% of butanediol monoacrylate, and 0.01% of butanediol diacrylate.

Example 4

The same procedure was performed as in Example 3, except that p-toluenesulfonic acid was used as the acid catalyst instead of sodium hydrogen sulfate. As a result, butanediol monoglycidyl ether acrylate was obtained with a purity of 98.2% and a yield of 97%. At the time, the resulting product contained 0.6% of butanediol monoglycidyl ether, 0.05% of butanediol monoacrylate, and 0.02% of butanediol diacrylate.

Comparative Example 1

Synthesis of Butanediol Monoglycidyl Ether Acrylate Using Butanediol as Starting Material A 1-L flask equipped with a stirrer, a thermometer, and a dropping funnel was charged with 300 g (3.3 moles) of 1,4-butanediol and 132 g (3.3 moles) of sodium hydroxide. After the temperature of the mixture was raised to 40° C. with stirring, 305 g (3.3 moles) of epichlorohydrin was gradually added to the mixture and allowed to react at a temperature controlled to 40 to 60° C. After the reaction for 3 hours, the reaction liquid was analyzed by gas chromatography. As a result, the degree of conversion of 1,4-butanediol was 45%. The reaction liquid was extracted five times with 600 g of water and 300 g of ethyl acetate. The organic phase was then washed twice with 200 g of water. The organic phase was concentrated by removing ethyl acetate by distillation using a rotary evaporator. The concentrate was then filtered, so that the desired product, butanediol monoglycidyl ether, was obtained with a purity of 87% and a yield of 41%. At the time, the resulting product contained 4% of butanediol and 5% of butanediol diglycidyl ether. Some other unknown components were also detected by gas chromatography. The product was further subjected to fractional distillation under reduced pressure (0.7 kPa). In the resulting product, the purity of butanediol monoglycidyl ether was 96.1%, and the contents of butanediol and butanediol diglycidyl ether were 1.2% and 2.1%, respectively. At the time, the distillation yield was 85%.

A 1-L flask equipped with a stirrer, a thermometer, an air-introducing tube, and a 15-stage rectifying tower was charged with 250 g of butanediol glycidyl ether synthesized as described above, 500 g of ethyl acrylate, and 0.1 g of p-methoxyphenol. While the pressure was controlled to 40 kPa and dry air was blown into the flask at a rate of 100 ml/minute, water was removed under reflux by heating until the content of water in the system reached about 300 ppm. Subsequently, 10 g of titanium tetraisopropoxide was added to start a reaction. During the reaction, the pressure in the system was controlled so that the reaction liquid temperature was about 95° C. The reaction was performed while the temperature of the top of the rectifying tower (tower top temperature) was monitored and while ethanol being produced and ethyl acrylate were removed as an azeotrope by distillation with the reflux ratio controlled at the azeotropic temperature of ethanol and ethyl acrylate. The temperature for azeotrope formation increased, and the ratio of distilled ethyl acrylate increased. After the reaction for 3 hours, therefore, the reaction liquid was analyzed by gas chromatography. As a result, the degree of conversion was 74.3%. From this state, almost no progress of the reaction was observed. Therefore, 10 g of titanium tetraisopropoxide was further added. As a result, the temperature for azeotrope formation decreased, and the reaction proceeded again. After the reaction was further allowed to proceed for 3 hours, the degree of conversion was determined to be 98.2% by gas chromatography analysis, and thus, the reaction was completed. After the reaction liquid was cooled, 30 g of water was added to hydrolyze the catalyst. The reaction liquid was then transferred into a 1-L eggplant-shaped flask. The excess ethyl acrylate and water was removed by distillation under reduced pressure using a rotary evaporator. The product was then purified by suction filtration, so that the desired product, butanediol monoglycidyl ether acrylate, was obtained with a purity of 94.6% and a yield of 94%. At the time, the resulting product contained 1.8% of butanediol monoglycidyl ether, 0.3% of butanediol monoacrylate, 0.9% of butanediol diacrylate, and 1.8% of butanediol diglycidyl ether. In gas chromatography analysis, peaks suggesting some by-products other than these compounds were also detected.

When the synthesis is started from 1,4-butanediol as in Comparative Example 1, butanediol diglycidyl ether and other by-products are produced, and a part of 1,4-butanediol is left as a residue. In the synthesis started from 1,4-butanediol, therefore, not only extraction needs to be performed twice or more, so that the process is complicated, but also the liquid finally obtained contains two or more different impurities.

The invention claimed is:

1. A method for producing an alkanediol glycidyl ether (meth)acrylate, the method comprising the steps of:
    subjecting a vinyloxyalkyl glycidyl ether to a devinylation reaction in the presence of an acid catalyst and water, thereby producing an alkanediol monoglycidyl ether and acetaldehyde;
    removing the acetaldehyde produced by the devinylation reaction while maintaining a reaction pressure at 50 kPa or less and a reaction temperature at 20 to 50° C., thereby obtaining the alkanediol monoglycidyl ether; and
    then performing a transesterification reaction of the alkanediol monoglycidyl ether with an alkyl(meth)acrylate.

2. The method according to claim 1, further comprising the step of adding an aqueous acid solution to perform an acetal decomposition reaction between the step of removing the acetaldehyde and the step of performing the transesterification reaction.

3. The method according to claim 1, further comprising the step of allowing a vinyl ether moiety-containing alcohol to react with an epihalohydrin to yield the vinyloxyalkyl glycidyl ether.

4. The method according to claim 3, wherein the vinyl ether moiety-containing alcohol is 4-hydroxybutyl vinyl ether.

5. The method according to claim 2, further comprising the step of allowing a vinyl ether moiety-containing alcohol to react with an epihalohydrin to yield the vinyloxyalkyl glycidyl ether.

* * * * *